Figure 1:
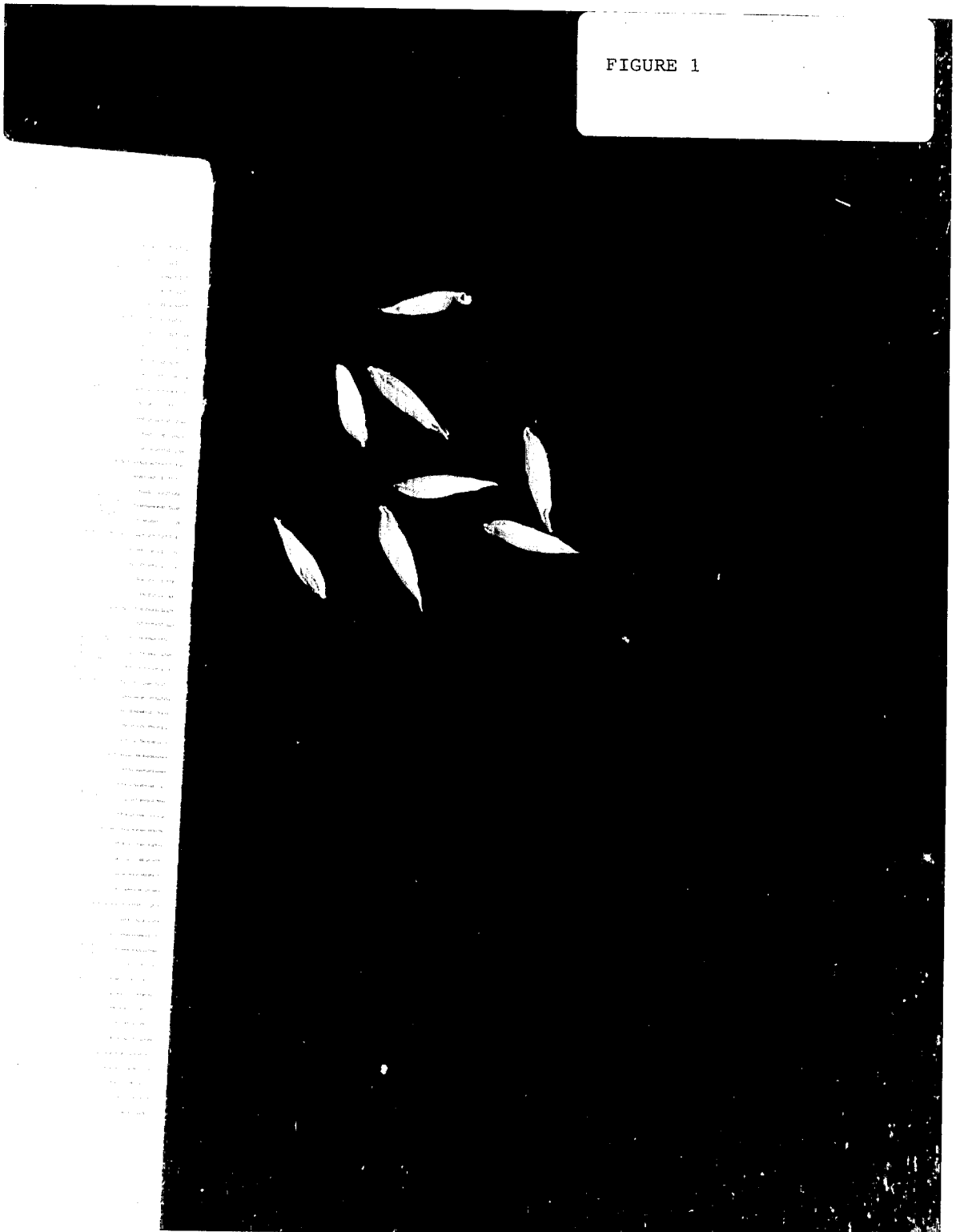

United States Patent [19]

Yensen

[11] Patent Number: Plant 6,459

[45] Date of Patent: Dec. 13, 1988

[54] SALTGRASS PLANT NAMED YENSEN 2

[75] Inventor: Nicholas P. Yensen, Tucson, Ariz.

[73] Assignee: Salt Weeds, Tucson, Ariz.

[21] Appl. No.: 901,316

[22] Filed: Aug. 28, 1986

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Cahill, Sutton & Thomas

[57] ABSTRACT

A grain variety of *Distichlis palmeri,* characterized by vigorous growth in salty soils, high grain yield and ideal form for harvest. This grain variety has excellent taste qualities.

1 Drawing Sheet

DESCRIPTION

The grain and plant described herein is related to the plant varieties described and illustrated in copending applications for plant patent filed by the present inventor entitled "Yensen 1" and "Yensen 3", assigned to the present assignee, filed concurrently herewith on Aug. 28, 1986 and assigned Ser. Nos. 901,315 and 901,204, respectively.

The present invention relates to a new and distinct variety of a plant of the family Poaceae and more particularly to a plant of the species *Distichlis palmeri* (Vasey) Fassett ex I. M. Johnston, commonly known as salt grass.

The accompanying drawing, FIG. 1, comprises a color photograph of the grain described herein.

This new variety was discovered at test plots of Salt Weeds (an Arizona partnership) in Tucson, Ariz.

The new variety was noted in test plantings wherein approximately 100,000 seeds, seedlings and cuttings had been test planted under agricultural conditions on a total of 2.5 acres following over ten (10) years of study of salt-tolerant plants. The purpose of these large plantings was specifically to discover new grain and plant varieties with commercial potential and to learn their agronomic requirements. The new variety resulted from a bad seedling.

Wild plants of *Distichlis palmeri* produce from near zero to four grams of grain per square meter. Yensen 1 can produce well over ten grams opf grain per square meter. The optimum yields with respect to fertilizer and water levels of Yensen 1 are not known at this time.

The new plant which first produced the new variety was first noted for its vigorous growth and ideal form and later for its high yield of grain on relatively short stalks. The stalks are erect and the grain heads are of a suitable height for combine harvest.

Plants of the new grain variety are being reproduced in Tucson, Ariz., where a number of other plant and grain varieties are slso being observed.

The new variety has a number of characteristics and desirable features distinguishing it as an improved variety. These characteristics are principally: a pleasing grain coloration of light brown which tends to be lighter posteriorly and darker anteriorly, high fertility and ideal grain habit suitable for harvest, including reduced shatter characteristics.

The following is a detailed description of the new variety:

Parentage: A grain variety Yensen-1, a plant variety of *Distichlis palmeri.*

Grain: 6–11 mm in length (including the bifurcation style), length decreasing slightly apically on the spikelet, 1–2 mm in width, 1–2 mm in height; embryo cover 2–4 mm in length; ventral surface indented with a longitudinal groove (except in unusually well-filled caryopses); anterior seed coat longitudinally wrinkled and posterior portion wrinkled into two rounded ventral keels and one rounded dorsal keel which extends to the bifurcation of the styles; surface texture with numerous longitudinal striae and light vertical rugae, glabrous, colored a coriaceous brown and tends to be darker anteriorly and lighter posteriorly (see FIG. 1).

Propagation: To date all grain (produced by plant variety Yensen-1) has held true to the distinguishing characteristics as described herein and it is expected that the grain will hold true to the distinguishing characteristics.

PLANT DESCRIPTION

Culms: Rigid, erect, occasionally branched, glabrous, 20–50 cm high depending on rhizome age at inflorescence, 2–3 mm in diameter.

Rhizomes: Thick and scaled at nodes.

Blades: Firm, rigid, ascending, pointed and pungent, involute (especially upon drying), distichous, glabrous to slightly puberulent, 3–5 mm basal width, 20–30 veins at base, typically 30–80 mm in length.

Sheath: Glabrous to slightly puberulent, with a tuft of wooly hairs at either side of the mouth, ligule smooth with pubescence apically.

Inflorescence:

*Panicle.*—Erect, compoundly branched (often branched in two's), 4–8 cm in length and does not extend beyond the leaves.

*Spikelet.*—With 5–9 flowers, subtending "bracts" infertile, 20–40 mm in length, 6–10 mm in width.

*Florets.*—Lemma 10–15 in length decreasing slightly apically on the spikelet, 4–6 feint veins on either side of a weak keel. Palea 9–11 mm in length, length decreasing slightly apically on the spikelet.

I claim:

1. A new and distinct grain variety of *Distichlis palmeri* as shown and described, which is principally characterized by a pleasing grain coloration grading from light brown posteriorly to dark brown anteriorly, reduced shatter characteristics, high grain fertilization rate, and a grain habit suitable for harvest.

* * * * *